(12) United States Patent
Dehestani

(10) Patent No.: US 11,786,838 B2
(45) Date of Patent: Oct. 17, 2023

(54) **METHODS FOR REMOVING PESTICIDES FROM *CANNABIS* PRODUCTS**

(71) Applicant: Cannacraft, Inc., Santa Rosa, CA (US)

(72) Inventor: Ahmad Dehestani, Walnut Creek, CA (US)

(73) Assignee: Cannacraft, Inc., Santa Rosa, CA (US)

( * ) Notice: Subject to any disclaimer, the term of this patent is extended or adjusted under 35 U.S.C. 154(b) by 222 days.

(21) Appl. No.: 17/075,246

(22) Filed: Oct. 20, 2020

(65) Prior Publication Data

US 2021/0291072 A1    Sep. 23, 2021

Related U.S. Application Data

(60) Provisional application No. 62/993,619, filed on Mar. 23, 2020.

(51) Int. Cl.
*B01D 11/02* (2006.01)
*A23L 33/105* (2016.01)
*A61K 31/352* (2006.01)
*A61K 9/00* (2006.01)
*A61K 45/06* (2006.01)

(52) U.S. Cl.
CPC ........ *B01D 11/0284* (2013.01); *A23L 33/105* (2016.08); *A61K 31/352* (2013.01); *B01D 11/0288* (2013.01); *A61K 9/007* (2013.01); *A61K 9/0014* (2013.01); *A61K 9/0043* (2013.01); *A61K 9/0056* (2013.01); *A61K 45/06* (2013.01)

(58) Field of Classification Search
CPC ............ B01D 11/0284; B01D 11/0288; A23L 33/105; A61K 31/352; A61K 9/00
See application file for complete search history.

(56) References Cited

U.S. PATENT DOCUMENTS

| | | |
|---|---|---|
| 4,877,530 A | 10/1989 | Moses |
| 8,481,085 B2 * | 7/2013 | Musty ............... A61K 45/06 424/725 |
| 11,000,818 B1 | 5/2021 | Sanchez |
| 2004/0143126 A1 | 7/2004 | Webster |
| 2006/0257463 A1 * | 11/2006 | Elsohly ............... A61K 9/1272 424/774 |
| 2007/0010700 A1 | 1/2007 | Bensmann |
| 2007/0093665 A1 | 4/2007 | Burdick |
| 2015/0297654 A1 | 10/2015 | Speier |
| 2017/0008870 A1 | 1/2017 | Dibble |
| 2018/0056211 A1 | 3/2018 | Seabrook |
| 2018/0085308 A1 * | 3/2018 | Renwick ............. A61K 9/0053 |
| 2018/0147247 A1 | 5/2018 | Ivanov |
| 2018/0193403 A1 | 7/2018 | George |
| 2019/0153484 A1 | 5/2019 | Bray |
| 2019/0240593 A1 | 8/2019 | Murphy |
| 2020/0054962 A1 | 2/2020 | Vanaman |
| 2020/0172503 A1 | 6/2020 | Oroskar |
| 2020/0215137 A1 | 7/2020 | Speier |
| 2021/0236955 A1 | 8/2021 | Dehestani |
| 2021/0275618 A1 | 9/2021 | Davidson |

FOREIGN PATENT DOCUMENTS

| | | |
|---|---|---|
| CA | 2455129 C | 10/2013 |
| CN | 104011218 A | 8/2014 |
| DE | 10106024 A1 | 8/2002 |
| WO | 2017184642 A1 | 10/2017 |

OTHER PUBLICATIONS

Hazekamp, The Trouble with CBD Oil, Medical Cannabis and Cannabinoids, Jun. 12, 2018, pp. 65-72, vol. 1, published by: S. Karger AG, Basel, Switzerland, published online.
English Translation of Raman patent publication Cn 104011216A, Aug. 27, 2014. (Year: 2014).

* cited by examiner

*Primary Examiner* — Sikarl A Witherspoon
(74) *Attorney, Agent, or Firm* — Innovation Law LLP

(57) ABSTRACT

Systems and methods for removing one or more pesticides from a *cannabis* product are provided. The method includes dissolving, in a solvent, a *cannabis* product including one or more pesticides, forming a dissolved solution, and cooling the dissolved solution to a cooling temperature, causing the *cannabis* product to precipitate from the dissolved solution, wherein, at the cooling temperature, the one or more pesticides remain dissolved in the dissolving solution. The method further includes removing the precipitated *cannabis* product from the dissolving solution. The disclosed method is suitable for removing one or more pesticides from various *cannabis* products containing natural cannabinoids, cannabinoids acetates, cannabinoid carboxylates, or the like.

25 Claims, No Drawings

METHODS FOR REMOVING PESTICIDES FROM CANNABIS PRODUCTS

CROSS-REFERENCE TO RELATED APPLICATIONS

This application claims priority under 35 U.S.C. § 119(e) to U.S. Provisional Patent Application No. 62/993,619, filed Mar. 23, 2020. The foregoing application is incorporated by reference herein in its entirety.

FIELD OF THE INVENTION

The present disclosure relates to methods of cleaning cannabis products and, in particular, to methods for removing pesticides from cannabis products, such as natural cannabinoids, cannabinoid acetates, and cannabinoid carboxylates.

BACKGROUND OF THE INVENTION

Cannabis products originate with commercially grown cannabis crops. As with many commercially grown crops, damage and destruction of the crop due to various pests and insects pose a threat to the crop. As a result of the threat of these pests, various forms of pesticides are often used in the production of cannabis. Even if the farmers growing the crop are not using pesticides, the crop may still come into contact with various pesticides.

Many cannabis products have come into contact with pesticides either from the farmers spraying the cannabis crop and/or from being infected by over-spraying on adjacent grow fields. This poses an issue for the sale of cannabis products having had contact with pesticides since the cannabis products cannot be sold or distributed with the pesticides still on them. Therefore, it is essential to remove the pesticides from cannabis products prior to distributing cannabis products in the marketplace.

There are several methods presently in use for removing pesticides from cannabis products. Some of these methods include the use of liquid chromatography. However, the high expenses associated with the methods make these methods cost-prohibitive. Additionally, these methods use a significant quantity of solvents and are limited in terms of which pesticides these methods can successfully remove.

For at least these reasons, a versatile and cost-effective means of removing pesticides from cannabis products is needed.

SUMMARY OF THE INVENTION

According to various embodiments of the present invention, a method for removing pesticide(s) from a cannabis product is provided. The disclosed method is suitable for removing one or more pesticides from various cannabis products containing natural cannabinoids, cannabinoids acetates, cannabinoid carboxylates, or the like.

The method includes acetylating or carboxylating a cannabis product (e.g., THC) and dissolving, in a solvent, the acetylated or carboxylated cannabis product including one or more pesticides, forming a dissolved solution, and cooling the dissolved solution to a cooling temperature, causing the cannabis product to precipitate from the dissolved solution, wherein, at the cooling temperature, the one or more pesticides remain dissolved in the dissolving solution. The method further includes removing the precipitated cannabis product from the dissolving solution.

In another aspect, this disclosure provides a method for removing one or more pesticides from an acetylated or carboxylated cannabis product (e.g., THCA). The method includes dissolving, in a solvent, an acetylated or carboxylated cannabis product (e.g., THCA) including one or more pesticides, forming a dissolved solution; cooling the dissolved solution to a cooling temperature to cause the cannabis product to precipitate from the dissolved solution, wherein, at the cooling temperature, the one or more pesticides remain dissolved in the dissolving solution; and removing the precipitated cannabis product from the dissolving solution.

In some embodiments, the method includes after removing the precipitated cannabis product from the dissolving solution, washing the precipitated cannabis product with the solvent one or more secondary times.

In some embodiments, the method includes removing any remaining solvent in a reduced pressure.

In some embodiments, the cooling temperature is between about 0° C. and about 100° C.

In some embodiments, the above steps are repeated to obtain the purified cannabis product with high purity, for example, a purity of about or above 85%, 95%, 98%, and 99%.

In some embodiments, the solvent includes one or more solvents selected from the group consisting of: hydrocarbons; aromatics; halogenated organic solvents; amines; and acetates. In some embodiments, the solvent can be pentane.

In another aspect, this disclosure provides a method for removing one or more pesticides from a cannabis product. The method comprises: (a) mixing a first solvent with a cannabis product comprising an acetylated or carboxylated cannabis product; (b) mixing the resulting solution with a second solvent comprising acetonitrile, thereby causing one or more pesticides to partition into a solvent layer containing the second solvent; and (c) removing the solvent layer containing the second solvent so that the resulting cannabis product contains a reduced amount of the one or more pesticides.

In some embodiments, the method further comprises repeating steps (a)-(c) at least once. In some embodiments, the first solvent comprises hexane. In some embodiments, the first solvent and the second solvent have a ratio of 1:2 (v/v).

In some embodiments, the cannabis product includes one or more cannabis products selected from the group consisting of: tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

In some embodiments of the present disclosure, the cannabis product is a distillate cannabis product.

In another aspect of this disclosure, also provided is a composition comprising the cannabis product with a reduced pesticide content prepared by the method as described above.

In some embodiments, the composition further comprises an additive, a pharmaceutical acceptable carrier, or an adjuvant to the cannabis component.

In some embodiments, the composition further comprises a second agent selected from the group consisting of: cannabinoids, terpenes, anti-insomnia, anti-tussive, opioid analgesic, decongestant, non-opioid analgesic/anti-inflammatory drug, anti-migraine drug, anti-emetic, anti-histamine, proton pump inhibitor, H2 antagonist/H2 blocker, tranquilizer, anticonvulsant, hypnotic, muscle relaxant, antipsychotic, anti-diarrheal, Attention Deficit and Hyperactivity Disorder (ADHD) drug, anti-Parkinson disease drug, benzodiazepine, benzodiazepine antagonist, barbiturate, barbiturate antagonist, stimulant, stimulant antagonist, antidepressant, nutraceutical, nicotine, BCS Class II active ingredient, BCS Class IV active ingredient, an anti-multiple sclerosis (MS) drug, ethyl pyruvate, melatonin, caffeine, resveratrol, and a combination thereof.

In some embodiments, the second agent is selected from the group consisting of: CBD, THC, CBN, CBG, CBC, THCA, CBDA, THCV, and a combination thereof.

In some embodiments, the composition is an oral dosage composition, a pulmonary or nasal dosage composition, or a topical dosage composition. In some embodiments, the composition is in the form of a solution, a spray, or a powder, a tablet, a capsule, a jelly, a cream, an ointment, a suspension, a spray or a chewing gum.

Also within the scope of this disclosure is a unit dose of the composition as described. The unit dose comprises: an amount of the composition selected from the group consisting of: trace amount, 0.01-0.05 mg, 0.05-0.1 mg, 0.1-0.5 mg, 0.25-1 mg, 0.5-15 mg, 0.5-2.5 mg, 1.0-2.5 mg, 2.5-5 mg, 5.0-7.5 mg, 5.0-10 mg, 1.0-25 mg, 25-50 mg, 50-75 mg, 75-100 mg, 10-20 mg, 10-15 mg, and 15-20 mg, 20-30 mg, 30-40 mg, 40-50 mg, 50-60 mg, 60-70 mg, 70-80 mg, 80-90 mg, 90-100 mg, 1-100 mg, 100-125 mg, 125-150 mg, 150-175 mg, 175-200 mg, and >200 mg.

In yet another aspect, this disclosure also provides a kit comprising the composition as described. The kit may further include a beverage. In some embodiments, the composition and the beverage are in separate containers.

Also provided is an edible product comprising the composition as described. The edible product can be one of a lozenge, candy, chocolate, brownie, cookie, trail bar, cracker, dissolving strip, pastry, bread, or chewing gum.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION OF THE INVENTION

Systems and methods for removing one or more pesticides from a *cannabis* product are provided. The disclosed systems and methods are suitable for removing one or more pesticides from various *cannabis* products containing, for example, natural cannabinoids, cannabinoids acetates, cannabinoid carboxylates, or the like.

A. METHODS FOR REMOVING PESTICIDES FROM *CANNABIS* PRODUCTS

The methods of the present disclosure include dissolving one or more *cannabis* products, having one or more pesticides coupled thereto, in one or more solvents in a liquid medium solution. The solvents are configured to dissolve the one or more *cannabis* products and the one or more pesticides.

Following the dissolution of the one or more *cannabis* products and the one or more pesticides, the solution including the solvents and the dissolved *cannabis* product is cooled to a temperature that enables the *cannabis* product to precipitate while maintaining that the one or more pesticides remain dissolved in the solution.

Following the precipitation of the *cannabis* product, the *cannabis* product is removed from the solution containing the one or more pesticides, isolating the *cannabis* product from the one or more pesticides. According to various embodiments, the isolated *cannabis* product is washed one or more additional times with cold solvent and, after each washing, the remaining solvent is removed under reduced pressure.

In some embodiments, the method starts with acetylating or carboxylating a *cannabis* product (e.g., THC) and dissolving, in a solvent, the acetylated or carboxylated *cannabis* product including one or more pesticides, forming a dissolved solution, and cooling the dissolved solution to a cooling temperature, causing the *cannabis* product to precipitate from the dissolved solution, wherein, at the cooling temperature, the one or more pesticides remain dissolved in the dissolving solution. The method further includes removing the precipitated *cannabis* product from the dissolving solution.

In some embodiments, the method starts directly from an acetylated or carboxylated *cannabis* product (e.g., THCA). The method includes dissolving, in a solvent, an acetylated or carboxylated *cannabis* product (e.g., THCA) including one or more pesticides, forming a dissolved solution; cooling the dissolved solution to a cooling temperature to cause the *cannabis* product to precipitate from the dissolved solution, wherein, at the cooling temperature, the one or more pesticides remain dissolved in the dissolving solution; and removing the precipitated *cannabis* product from the dissolving solution.

According to various embodiments, the *cannabis* product includes a distillate *cannabis* material. The distillate *cannabis* material may have low solubility in organic solvents such as, but not limited to, pentane. According to various embodiments, the solvent has a high solubility of the one or more pesticides at a particular temperature range. The temperature range may be from approximately 0 to 100 degrees Celsius. For example, this temperature can be about 10 degrees C., about 20 degrees C., about 30 degrees C., about 40 degrees C., about 45 degrees C., about 50 degrees C., about 55 degrees C., about 60 degrees C., about 65 degrees C., about 70 degrees C., about 75 degrees C., about 80 degrees C., or in the range of 60-80 degrees C., 65-75 degrees C., 55-85 degrees C., and the like.

The solvent or solvents may include hydrocarbons, aromatics, halogenated organic solvents, amines, acetates, and/or any other suitable solvents.

The *cannabis* products may include, but are not limited to, cannabidiol ("CBD"), cannabidiolic acid ("CBDA"), tetrahydrocannabinolic acid ("THCA"), cannabinolic acid ("CBNA"), cannabigerolic acid ("CBGA"), tetrahydrocannabinolic acid ("THCA"), and/or all other carboxylate *cannabis* material and/or their acetate as well as both of their forms.

According to an illustrative example, a sample of CBD with a pesticide is dissolved in acetonitrile. Once the CBD and pesticide are dissolved, the solvent is removed under reduced pressure. According to the illustrative example, the pesticide and CBD, approximately 10 grams, is dissolved in a minimal amount of pentane, approximately 20 mL. Once dissolved, the solution is cooled to a cooling temperature. The cooling temperature may be any suitable cooling temperature. According to the illustrative example, the cooling temperature is approximately 40 degrees Celsius.

Cooling the solution to the cooling temperature causes the CBD to precipitate. The precipitated CBD is then filtered from the solution containing the dissolved pesticide. According to the illustrative embodiment, the filtered clean CBD is washed two more times with cold pentane (e.g., 10 mL at 40 degrees Celsius). The CBD is then removed from the solvent under reduced pressure that has been tested for pesticides. According to an embodiment, the yield is approximately 95% recovery of the original amount of the CBD, with a shown reduction in the number of pesticides from the original amounts. If needed, more washing of the CBD may be performed to remove more of the pesticides.

According to various embodiments, the above-illustrated example may be performed wherein the *cannabis* product is THCA, CBDA, CBGA, and/or all carboxylate *cannabis* material.

According to various embodiments, the above-illustrated example may be performed wherein the solvent is an acetate.

This disclosure also provides an alternative method of removing pesticides. For example, pesticides may be removed by employing a solvent system comprising one or more solvents in which pesticides exhibit higher solubility than an acetylated or carboxylated *cannabis* product(s), e.g., THCA.

The solvent system can be formed of one or more solvents that are added to the *cannabis* products in a step-wise fashion. In one example, the solvent system comprises a firt solvent, e.g., hexane and a second solvent, e.g., acetonitrile. Hexane/acetonitrile are non-miscible and used in this example. Hexane and acetonitrile have different solubility for *cannabis* materials and pesticides. For example, most pesticides more soluble in acetonitrile than in hexane. In some embodiments, the method includes contacting the *cannabis* product with the first solvent, followed by adding and mixing the second solvent.

In some embodiments, the method for removing one or more pesticides from a *cannabis* product comprises: (a) mixing a first solvent with a *cannabis* product comprising an acetylated or carboxylated *cannabis* product; (b) mixing the resulting solution with a second solvent comprising acetonitrile, thereby causing one or more pesticides to partition into a solvent layer containing the second solvent; and (c) removing the solvent layer containing the second solvent so that the resulting *cannabis* product contains a reduced amount of the one or more pesticides.

In some embodiments, the method further comprises repeating steps (a)-(c) at least once. In some embodiments, the first solvent comprises hexane. In some embodiments, the first solvent and the second solvent have a ratio of 1:2 (v/v) (e.g., 3:1, 2:1, 1:1, 1:1:1.5, 1:2, 1:2.5, 1:3, 1:3.5, 1:4, 1:4.5, 1:5).

While certain embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure.

In related embodiments, the one or more pesticides can be removed by solvent partition using a solvent system comprising two or more solvents. For example, the solvent system may include hexane and acetonitrile that do not mix but both dissolve the oil and pesticides. Since pesticides have a higher solubility in acetonitrile, they will be partitioned primarily in the acetonitrile phase. The cannabinoids have a higher solubility in hexane and thus are primarily partitioned in the hexane phase. The solvent partition process can be repeated one or more times until a desired purity of cannabinoids is yielded. The solvent partition process can be performed alone or in combination with the methods described above. For example, the solvent partition process can be carried out before or after the above-described methods to obtain *cannabis* products with minimal contamination of pesticides.

B. COMPOSITIONS, KITS, AND METHODS OF USE

In another aspect of this disclosure, also provided is a composition comprising the *cannabis* product with a reduced pesticide content prepared by the method as described above. The composition further comprises an additive, a pharmaceutical acceptable carrier, or an adjuvant to the *cannabis* component.

The composition can be an oral dosage composition, a pulmonary or nasal dosage composition, or a topical dosage composition. The compositions can be in the form of a solution, a spray, or a powder. In some embodiments, the composition is in the form of a tablet, a capsule, a jelly, a cream, an ointment, a suspension, a spray or a chewing gum.

In certain embodiments, the compositions as described herein are administered via a vaporizer or like device as described, for example, in U.S. Pat. No. 8,915,254; U.S. Pat. Appl. Pub. No. 2014/0060552; U.S. Pat. No. 8,488,952; and U.S. Pat. Appl. Pub. No. 2015/0040926. Compositions for pulmonary administration also include, but are not limited to, dry powder compositions consisting of the powder of a *cannabis* oil described herein, and the powder of a suitable carrier and/or lubricant. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

Pharmaceutical compositions or medicaments can be formulated by standard techniques or methods well-known in the art of pharmacy using one or more physiologically acceptable carriers or excipients. Suitable pharmaceutical carriers are described herein and in, e.g., "Remington's Pharmaceutical Sciences" by E. W. Martin. *Cannabis* oil extracts can be formulated for administration by any suitable route, including, but not limited to, orally, topically, nasally, rectally, vaginally, pulmonary, parenterally (e.g., intravenously, subcutaneously, intramuscularly, etc.), and combinations thereof. In some embodiments, the *cannabis* oil is diluted in a liquid, e.g., a carrier oil. The most suitable route of administration in any given case will depend in part on the condition being treated as well as the response of the subject to the particular route of treatment.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, maltodextrin, lecithin, agarose, xanthan gum, guar gum, sorbitol, cellulose (e.g., ethyl cellulose, microcrystalline cellulose), glycine, pectin, polyacrylates and/or calcium hydrogen phosphate, calcium sulfate, (b) lubricants; e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium or potassium salt, or effervescent mixtures; (e) wetting agents, e.g., sodium lauryl sulfate, and/or (f) absorbents, colorants, flavors, and sweeteners. Tablets can be either uncoated or coated according to methods known in the art. The excipients described herein can also be used for preparation of buccal dosage forms and sublingual dosage forms (e.g., films and lozenges) as described, for example, in U.S. Pat. Nos. 5,981,552 and 8,475,832. Formulation in chewing gums as described, for example, in U.S. Pat. No. 8,722,022, is also contemplated.

Further preparations for oral administration can take the form of, for example, solutions, syrups, suspensions, and toothpastes. Liquid preparations for oral administration can be prepared by conventional means with pharmaceutically acceptable additives, for example, suspending agents, for example, sorbitol syrup, cellulose derivatives, or hydrogenated edible fats; emulsifying agents, for example, lecithin, xanthan gum, or acacia; non-aqueous vehicles, for example, almond oil, sesame oil, hemp seed oil, fish oil, oily esters, ethyl alcohol, or fractionated vegetable oils; and preservatives, for example, methyl or propyl-p-hydroxybenzoate or sorbic acid. The preparations can also contain buffer salts, flavoring, coloring, and/or sweetening agents as appropriate.

Typical formulations for topical administration include creams, ointments, sprays, lotions, hydrocolloid dressings, and patches, as well as eye drops, ear drops, and deodorants. *Cannabis* oils can be administered via transdermal patches as described, for example, in U.S. Pat. Appl. Pub. No. 2015/0126595 and U.S. Pat. No. 8,449,908. Formulation for rectal or vaginal administration is also contemplated. The *cannabis* oils can be formulated, for example, using suppositories containing conventional suppository bases such as cocoa butter and other glycerides as described in U.S. Pat. Nos. 5,508,037 and 4,933,363. Compositions can contain other solidifying agents such as shea butter, beeswax, kokum butter, mango butter, illipe butter, tamanu butter, carnauba wax, emulsifying wax, soy wax, castor wax, rice bran wax, and candelilla wax. Compositions can further include clays (e.g., Bentonite, French green clays, Fuller's earth, Rhassoul clay, white kaolin clay) and salts (e.g., sea salt, Himalayan pink salt, and magnesium salts such as Epsom salt).

The compositions set forth herein can be formulated for parenteral administration by injection, for example, by bolus injection or continuous infusion. Formulations for injection can be presented in unit dosage form, for example, in ampoules or in multi-dose containers, optionally with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure, buffers, and/or other ingredients. Alternatively, the compositions can be in powder form for reconstitution with a suitable vehicle, for example, a carrier oil, before use. In addition, the compositions may also contain other therapeutic agents or substances.

The compositions can be prepared according to conventional mixing, granulating, and/or coating methods, and contain from about 0.1 to about 75%, preferably from about 1 to about 50%, of the *cannabis* oil extract. In general, subjects receiving a *cannabis* oil composition orally are administered doses ranging from about 1 to about 2000 mg of *cannabis* oil. A small dose ranging from about 1 to about 20 mg can typically be administered orally when treatment is initiated, and the dose can be increased (e.g., doubled) over a period of days or weeks until the maximum dose is reached.

In some embodiments, the composition is an oral dosage composition, a pulmonary or nasal dosage composition, or a topical dosage composition. The composition may be in the form of a solution, a spray, or a powder, a tablet, a capsule, a jelly, a cream, an ointment, a suspension, a spray or a chewing gum.

Also within the scope of this disclosure is a unit dose of the composition as described above. In some embodiments, the unit dose comprises an amount of the composition selected from the group consisting of: trace amount, 0.01-0.05 mg, 0.05-0.1 mg, 0.1-0.5 mg, 0.25-1 mg, 0.5-15 mg, 0.5-2.5 mg, 1.0-2.5 mg, 2.5-5 mg, 5.0-7.5 mg, 5.0-10 mg, 1.0-25 mg, 25-50 mg, 50-75 mg, 75-100 mg, 10-20 mg, 10-15 mg, and 15-20 mg, 20-30 mg, 30-40 mg, 40-50 mg, 50-60 mg, 60-70 mg, 70-80 mg, 80-90 mg, 90-100 mg, 1-100 mg, 100-125 mg, 125-150 mg, 150-175 mg, 175-200 mg, and >200 mg.

In some embodiments, the composition may further comprise a second agent selected from the group consisting of: cannabinoids, terpenes, anti-insomnia, anti-tussive opioid analgesic, decongestant, non-opioid analgesic/anti-inflammatory drug, anti-migraine drug, anti-emetic, anti-histamine, proton pump inhibitor, H2 antagonist/H2 blocker, tranquilizer, anticonvulsant, hypnotic, muscle relaxant, antipsychotic, anti-diarrheal, Attention Deficit and Hyperactivity Disorder (ADHD) drug, anti-Parkinson disease drug, benzodiazepine, benzodiazepine antagonist, barbiturate, barbiturate antagonist, stimulant, stimulant antagonist, antidepressant, nutraceutical, nicotine, BCS Class II active ingredient, BCS Class IV active ingredient, an anti-multiple sclerosis (MS) drug, ethyl pyruvate, melatonin, caffeine, resveratrol, and a combination thereof.

In some embodiments, the second agent is selected from the group consisting of: CBD, THC, CBN, CBG, CBC, THCA, CBDA, THCV, and a combination thereof.

In some embodiments, the composition at therapeutically effective concentrations or dosages can be combined with a pharmaceutically or pharmacologically acceptable carrier, excipient or diluent, either biodegradable or non-biodegradable.

For example, the composition may be administered in the pure form or in a pharmaceutically acceptable formulation including suitable elixirs, binders, and the like (also generally referred to a "carriers") or as pharmaceutically acceptable salts (e.g., alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil-based vehicles. Water may be used as the carrier for the preparation of compositions (e.g., injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc.). Solid diluents and excipients include lactose, starch, conventional disintegrating agents, coatings, and the like. Preservatives such as methylparaben or benzalkonium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

Examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly (malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropyl cellulose, hydroxypropylmethylcellulose phthalate, noncrystalline cellulose, magnesium aluminum silicate, triethanolamine, polyvinyl alcohol, polyvinylpyrrolidone, sugars, and starches. See, for example, Remington: The Science and Practice of Pharmacy, 1995, Gennaro ed.

In some embodiments, the chemicals can be purified and blended together to produce a formulation similar in form to that for Marinol®. In these formulations, the active ingredient is dissolved in sesame seed oil or similar oil and enclosed in a gel-capsule. In other embodiments, the formulation may be arranged to be used as an injectable or as an aerosol. In these embodiments, as will be apparent to one of skill in the art, the appropriate pharmaceutically-acceptable additives may be added so that the pharmaceutical composition is in the appropriate form.

As will be appreciated by one knowledgeable in the art, the formulation may be used as, for example, an anti-emetic, appetite stimulant, or as a treatment for nausea, dementia, Alzheimer's disease, glaucoma, high blood pressure, inflammation or multiple sclerosis. For example, when administered to an individual in need of such treatment, the pharmaceutical composition of $\Delta^8$-THC and CBD will accomplish at least one of the following: reduce nausea, promote or stimulate appetite, reduce vomiting and/or promote a general feeling of well-being.

Additional Ingredients

Cannabinoids are susceptible to oxidation and hydrolysis. Over time it is possible for cannabinoids to be exposed to oxygen, hydrogen ions (acids, water), in addition to any other environmental factors that will cause their degradation.

Organic bases can be used to prevent the degradation of the cannabinoids. These organic bases include, but are not limited to, butyl hydroxyl anisole (BHA), butyl hydroxyl toluene (BHT) and sodium ascorbate; at concentrations between 0.001 to 5%>w/w, for example. Organic bases such as the following can improve the stability of cannabinoids from chemical degradation for up to 2 years: BHA 0.001 to 5% w/w, BHT 0.001 to 5% w/w, and combinations of BHA and BHT can also be used.

Antioxidants can be used to prevent or at least inhibit or mitigate the degradation of cannabinoids from oxidation. Examples of antioxidants include: ethanol, polyethylene glycol 300, polyethylene glycol 400, propylene glycol, propylene carbonate, N-methyl-2-pyrrolidones, dimethylacetamide, dimethyl sulfoxide, hydroxypropyl-P-cyclodextrins, sulfobutylether-β-cyclodextrin, a-cyclodextrin, HSPC phospholipid, DSPG phospholipid, DMPC phospholipid, DMPG phospholipid, ascorbyl palmitate, butylated hydroxyanisole, butylated hydroxyanisole, propyl gallate, a-tocopherol, γ-tocopherol, propyl gallate, lecithin, Vitamin E tocopherol, sesamin, sesamol, sesamolin, alpha-tocopherol, ascorbic acid, ascorbyl palmitate, fumaric acid, malic acid, sodium metabisulfite, and EDTA. Specific antioxidant examples include, but are not limited to: Ascorbic Acid: 0.001 to 5% w/w, Vitamin E Tocopherol: 0.001 to 5% w/w, Tocopherol: 0.001 to 5% w/w, and combinations of ascorbic acid, vitamin E tocopherol, and tocopherol can be used for this invention.

Chelating agents can prevent or at least mitigate the degradation of cannabinoids from metal ions in solution. Chelating agents include, but are not limited to, ethylenediaminetetraacetic acid (EDTA), phosphoric acid, polyphosphates, polysaccharides, citric acid and any combination thereof.

Preservatives can be used to prevent microbial spoilage. These preservatives include: methylparabens, ethylparabens, propylparabens, butylparabens, sorbic acid, acetic acid, propionic acid, sulfites, nitrites, sodium sorbate, potassium sorbate, calcium sorbate, benzoic acid, sodium benzonate, potassium benzonate, calcium benzonate, sodium metabisulfite, propylene glycol, benzaldehyde, butylated hydroxytoluene, butylated hydroxyanisole, formaldehyde donors, essential oils, citric acid, monoglyceride, phenol, mercury components and any combination thereof. Specific examples include, but are not limited to, sodium benzoate and potassium sorbate.

Additionally, the pH can be lowered to prevent or retard microbial growth. Lowering the pH below 4.0 is sufficiently low enough to prevent microbial growth for a minimum of 1 month.

Preservatives and/or stabilizers can be added during formulation. Depending on the nature of the preservative/stabilizer, it may be contained in either the oil phase, interfacial layer, or the aqueous continuous phase. Once dissolved the preservatives and stabilizers are released into solution imparting their properties into the aqueous system. This allows beverage manufacturers the ability to instantly create shelf-stable *cannabis*-infused beverages. Beverages made this way can resist microbial growth and chemical degradation for a minimum of 3 months.

The composition can be used for treatment of a subject afflicted with or suffering from nausea, muscular spasms, multiple sclerosis, uterine cramps, bowel cramps, a movement disorder, pain, migraine headache, vertigo, glaucoma, asthma, inflammation, insomnia, high blood pressure, cancer, anxiety, convulsions, depression or psychosis.

Accordingly, in another aspect, this disclosure provides a method of treatment of a subject. The method comprises administering to a subject afflicted with or suffering from nausea, muscular spasms, multiple sclerosis, uterine cramps, bowel cramps, a movement disorder, pain, migraine headache, vertigo, glaucoma, asthma, inflammation, insomnia, high blood pressure, cancer, anxiety, convulsions, depression or psychosis, an effective amount of the composition as described above.

In some embodiments, the composition is administered intratumorally, intravenously, subcutaneously, intraosseously, orally, transdermally, in sustained release, in controlled release, in delayed release, as a suppository, or sublingually. In some embodiments, the composition is administered once, twice, three, or four times per day, or as needed.

The administration of the composition invention may be intermittent, bolus dose, or at a gradual or continuous, constant or controlled rate to a patient. In addition, the time of day and the number of times per day that the pharmaceutical formulation is administered may vary and are best determined by a skilled practitioner such as a physician. Further, the effective dose can vary depending upon factors such as the mode of delivery, gender, age, and other conditions of the patient, as well as the extent or progression of the disease. The compounds may be provided alone, in a mixture containing two or more of the compounds, or in combination with other medications or treatment modalities. The compounds may also be added to blood ex vivo and then be provided to the patient.

In one aspect, this disclosure provides a kit comprising the composition as described above. In some embodiments, the kit further comprising a beverage, wherein the composition and the beverage are in separate containers. In some embodiments, the kit may further include instructional materials.

"Instructional material," as that term is used herein, includes a publication, a recording, a diagram, or any other medium of expression that can be used to communicate the usefulness of any composition and/or compound of the invention in a kit. The instructional material of the kit may, for example, be affixed to a container that contains any composition of the invention or be shipped together with a container which contains any composition. Alternatively, the instructional material may be shipped separately from the container with the intention that the recipient uses the instructional material and any composition cooperatively. Delivery of the instructional material may be, for example, by physical delivery of the publication or other medium of expression communicating the usefulness of the kit, or may alternatively be achieved by electronic transmission, for example, by means of a computer, such as by electronic mail, or download from a website.

Also within the scope of this disclosure is an edible product comprising the composition as described above. In some embodiments, the edible product is selected from a lozenge, candy, chocolate, brownie, cookie, trail bar, cracker, dissolving strip, pastry, bread, or chewing gum.

C. DEFINITIONS

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The term "*cannabis*" refers to plants of the genus *cannabis*, including *Cannabis saliva, Cannabis indica*, and *Cannabis ruderalis*.

The term "*cannabis* oil" refers to a mixture of compounds obtained from the extraction of *cannabis* plants. Such compounds include, but are not limited to, cannabinoids, terpenes, terpenoids, and other compounds found in the *cannabis* plant. The exact composition of *cannabis* oil will depend on the strain of *cannabis* that is used for extraction, the efficiency and process of the extraction itself, and any additives that might be incorporated to alter the palatability or improve administration of the *cannabis* oil.

The term "cannabinoid" refers to a chemical compound that shows direct or indirect activity at a cannabinoid receptor. There are two main cannabinoid receptors, CNR1 (also known as CB1) and CNR2 (also known as CB2). Other receptors that research indicates have cannabinoid activity include the GPR55, GPR18, and TRPV1 receptors. The term "phytocannabinoid" refers to cannabinoids that occur in a plant species or are derived from cannabinoids occurring in a plant species. Examples of cannabinoids include, but are not limited to, tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

As used herein, CBD refers to cannabidiol.

As used herein, $\Delta^9$-THC refers to $\Delta^9$-tetrahydrocannabinol.

As used herein, $\Delta^8$-THC refers to $\Delta^8$-tetrahydrocannabinol.

The term "acidic cannabinoid" refers to a cannabinoid having one or more carboxylic acid functional groups. Examples of acidic cannabinoids include, but are not limited to, tetrahydrocannabinolic acid (THCA), cannabidiolic acid (CBDA), and cannabichromenic acid (CBC). Acidic cannabinoids are frequently the predominant cannabinoids found in raw (i.e., unprocessed) *cannabis* plant material.

The term "essential oil" refers to natural plant oil typically obtained by distillation and having a chemical composition and organoleptic properties (e.g., fragrance) characteristic of the plant or other sources from which it is extracted.

As used herein, "anti-emetic" refers to compounds capable of reducing nausea, enhancing appetite and/or reducing vomiting in an individual.

The term "water-soluble," as used herein, refers to that 1 mg of material in 1 ml of water gives a clear solution and is water-miscible.

The term "high affinity," as used herein, refers to that the compounds exhibit a Ki in the range of about 0.03 nM to about 80 nM, and preferably from about 0.03 nM to about 50 nM, for either the CB1 or CB2 receptors, or both.

As used herein, "effective amount" refers to the administration of an amount of a given compound that achieves the desired effect. For example, regarding the combination of CBD and $\Delta^8$-THC, an "effective amount" is an amount sufficient for or that is capable of reducing nausea or vomiting and/or enhancing appetite in a patient or individual in need of such treatment. The patient may be a human patient.

As used herein, "purified" does not require absolute purity but is instead intended as a relative definition. For example, purification of starting material or natural material to at least one order of magnitude, preferably two or three orders of magnitude is expressly contemplated as falling within the definition of "purified."

As used herein, the term "isolated" requires that the material be removed from its original environment.

As used herein, the terms "subject" and "patient" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc) and a human). The subject may be a human or a non-human. In this context, a "normal," "control," or "reference" subject, patient or population is/are one(s) that exhibit(s) no detectable disease or disorder, respectively.

"Sample," "test sample," and "patient sample" may be used interchangeably herein. The sample can be a sample of, serum, urine plasma, amniotic fluid, cerebrospinal fluid, cells (e.g., antibody-producing cells) or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

The term "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

The terms "prevent," "preventing," "prevention," "prophylactic treatment" and the like refer to reducing the probability of developing a disorder or condition in a subject (e.g., plant), who does not have, but is at risk of or susceptible to developing a disorder or condition.

The terms "decrease," "reduced," "reduction," "decrease," or "inhibit" are all used herein generally to mean a decrease by a statistically significant amount. However, for avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

The section headings as used herein are for organizational purposes only and are not to be construed as limiting the subject matter described.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

D. EXAMPLES

Example 1

A sample of pesticide clean CBD dissolved in acetonitrile. The sample is deliberately done with known amounts of all pesticides that the government is currently testing. The solvent is removed under reduced pressure and tested (Table 2). The CBD infected material, 10 grams, dissolved in a minimal amount of pentane, 20 mL, then cooled −40 C. The material is then filtered, and the solid clean CBD is washed two more times with cold pentane, 10 mL at 40 C. The CBD is then removed of any solvent under reduced pressure tested for pesticides. The yield is 95% recovery of the CBD original amount. All pesticides show reductions in the amount from the original (Table 1). All of the pesticides have been removed by over 75%. If more remained, then another washing is needed in the samples.

Example 2

Please provide experimental details for removing pesticides from acetylated or carboxylated *cannabis* products, such as THCA. A sample of 10 grams THCATHC material is deliberately spiked with pesticides in ethanol 20 mL. It is mixed well, and the sample is tested. Then 100 mL of acetonitrile is added mixed vigorously. The acetonitrile is removed by pouring off. Then another 100 mL of acetonitrile is added and vigorously mixed again. The material is rotovated to remove any more solvent. Then the material is tested (Table 3), and all of the pesticides have been removed. The amount of THC is lowered, but all of the THCA remains.

Example 3

If the material is such that it does dissolve in acetonitrile such as THC, then it can first be carboxylated, then the same procedures as Example 2 can be run. To carboxylate the material, the following could be used.

1) make 0.1 Molar NaOH in anhydrous ethanol
2) add 4 A sieves to
3) add 1:1 eq THC/sodium ethoxide
4) rotavapor all the way down
5) scrape off the crystals and put into the pressure reactor with a stir par
6) add 500 psi of $CO_2$
7) heat in oil bath at 90 C for one day with stirring
8) open the reactor
9) dissolve the mixture in hexane
10) add dilute sulfuric acid until the pH in neutral
11) put into a separation funnel
12) remove the bottom water layer
13) wash three times with brine solution and remove the water every time
14) Rotavapor off the solvent.

The yield ranges from 50-87% conversion to the carboxylate

Example 4

This disclosure also provides an alternative method of removing pesticides. For example, pesticides may be removed by employing a solvent system comprising one or more solvents in which pesticides exhibit higher solubility than an acetylated or carboxylated *cannabis* product(s), e.g., THCA.

The solvent system can be formed of one or more solvents that are added to the *cannabis* products in a step-wise fashion. In one example, the solvent system comprises a first solvent, e.g., hexane and a second solvent, e.g., acetonitrile. Hexane/acetonitrile are non-miscible and used in this example. Hexane and acetonitrile have different solubility for *cannabis* materials and pesticides. For example, most pesticides more soluble in acetonitrile than in hexane. In some embodiments, the method includes contacting the *cannabis* product with the first solvent, followed by adding and mixing the second solvent.

As shown in Table 4, 20 grams of dirty oil was dissolved in 150 mL of hexane, followed by adding 300 mL of acetonitrile (or $CH_3CN$). Put both into a separate funnel and mix then let sit. Take off the acetonitrile bottom layer rotovap and put aside. This layer has the majority of the pesticides in it. After rotovaping the hexane layer, the sample thereof was subjected to analysis. The results show that the pesticide content was significantly reduced, and potency was significantly increased. If needed, the *cannabis* product can be further purified by repeating the steps as described above. For example, the *cannabis* product was mixed with 150 mL of hexane, followed by adding and mixing 300 mL of acetonitrile. The results of sample testing were provided in Table 4, which shows further improved purity and potency of the resulting *cannabis* products.

TABLE 1

Cleaned spike CBD after one wash, with all of the pesticides reduced.

Report of Analysis Revision

| | | |
|---|---|---|
| Manufacturer: | | |
| Manufacturer Address: | | |
| Manufacturer License #: | | |
| Report #: | | |
| Sample Code: | CRFT Manufacturing | |
| Dates of Analysis: | 2330 Circadian Way, Santa Rosa, CA | 95407 |

TABLE 1-continued

Cleaned spike CBD after one wash, with all of the pesticides reduced.

Report of Analysis Revision

| | |
|---|---|
| Sample Matrix: | CDPH-T00000329 |
| Sample Name: | N9944 6649 May 15, 2019-May 17, 2019 |
| Percent Moisture (%) | N/A |
| SOP: [SLW-MCWA] Moisture Analyzer | CLEAN CBD |
| Water Activity ($A_w$) SOP: [SLW-MCWA] Moisture Analyzer | |
| Pesticide Screen Result-Category 1 [SLW-PA] | NT |
| Target Analyte PPM LOD LOQ Pass/Fail | NT |

Pesticide Screen Category 1 – California Limit – Detect/No Detect All products

| Analyte | Target | PPM | PPM | Pass/Fail |
|---|---|---|---|---|
| Aldicarb | NT | $0.65 A_w$ | | NT |
| Carbofuran | | | | |
| Chlordane | | | | |
| Chlorfenapyr | | | | |
| Chlorpyrifos | 0.1 | 0.05 | 0.10 | Fail |
| Coumaphos | 0.2 | 0.05 | 0.10 | Fail |
| Daminozide | ND | 0.05 | 0.10 | Pass |
| Dichlorvos | ND | 0.05 | 0.10 | Pass |
| Dimethoate | 0.1 | 0.05 | 0.10 | Fail |
| Ethoprop(hos) | 0.2 | 0.05 | 0.10 | Fail |
| Etofenprox | 1.2 | 0.05 | 0.10 | Fail |
| Fenoxycarb | 0.5 | 0.05 | 0.10 | Fail |
| Fipronil | 0.2 | 0.05 | 0.10 | Fail |
| Imazalil | 0.3 | 0.05 | 0.10 | Fail |
| Methiocarb | 0.1 | 0.05 | 0.10 | Fail |
| Methyl Parathion | 0.2 | 0.05 | 0.10 | Fail |
| Mevinphos | 0.1 | 0.05 | 0.10 | Fail |
| Paclobutrazol | 0.1 | 0.05 | 0.10 | Fail |
| Propoxur | 0.2 | 0.05 | 0.10 | Fail |
| Spiroxamine | ND | 0.05 | 0.10 | Pass |
| Thiacloprid | 0.2 | 0.05 | 0.10 | Fail |
| | 0.1 | 0.05 | 0.10 | Fail |
| Pesticide Screen Category 2 [SLW-PA] | 0.2 | 0.05 | 0.10 | Fail |
| | 0.1 | 0.05 | 0.10 | Fail |
| Target Analyte PPM PPM Pass/Fail PPM Pass/Fail | 0.2 | 0.05 | 0.10 | Fail |

Pesticide Screen Category 2 – California Limit – Inhaled Product / Non-Inhaled Product

| Analyte | PPM | Inhaled PPM | Pass/Fail | Non-Inhaled PPM | Pass/Fail |
|---|---|---|---|---|---|
| Acephate | | | | | |
| Acequinocyl | | | | | |
| Acetamiprid | | | | | |
| Avermectin B1a (Abamectin) | | | | | |
| Avermectin B1b (Abamectin) | 0.15 | 0.10 | Fail | 5.0 | Pass |
| Azoxystrobin | ND | 0.10 | Pass | 4.0 | Pass |
| Bifenazate | 0.16 | 0.10 | Fail | 5.0 | Pass |
| Bifenthrin | 0.78 | 0.10 | Fail | 0.3 | Fail |
| Boscalid | 0.67 | 0.10 | Fail | 0.3 | Fail |
| Captan | 0.21 | 0.10 | Fail | 40.0 | Pass |
| Carbaryl | 0.11 | 0.10 | Fail | 5.0 | Pass |
| Chlorantraniliprole | 0.04 | 3.00 | Pass | 0.5 | Pass |
| Clofentezine | 0.11 | 0.10 | Fail | 10.0 | Pass |
| Cyfluthrin | ND | 0.70 | Pass | 5.0 | Pass |
| Cypermethrin | 0.70 | 0.50 | Fail | 0.5 | Fail |
| Diazinon | 0.98 | 10.00 | Pass | 40.0 | Pass |
| Dimethomorph | 0.08 | 0.10 | Pass | 0.5 | Pass |
| Etoxazole | ND | 2.00 | Pass | 1.0 | Pass |
| Fenhexamid | ND | 1.00 | Pass | 1.0 | Pass |
| Fenpyroximate | 0.10 | 0.10 | Fail | 0.2 | Pass |
| Flonicamid | 0.17 | 2.00 | Pass | 20.0 | Pass |
| Fludioxonil | 0.04 | 0.10 | Pass | 1.5 | Pass |
| Hexythiazox | 0.11 | 0.10 | Fail | 10.0 | Pass |
| Imidacloprid | 0.20 | 0.10 | Fail | 2.0 | Pass |
| Kresoxim-methyl | 0.14 | 0.10 | Fail | 2.0 | Pass |
| Malathion | 0.19 | 0.10 | Fail | 30.0 | Pass |

TABLE 1-continued

Cleaned spike CBD after one wash, with all of the pesticides reduced.

Report of Analysis Revision

| | | | | | |
|---|---|---|---|---|---|
| Metalaxyl | 0.14 | 0.10 | Fail | 2.0 | Pass |
| Methomyl | 0.15 | 5.00 | Pass | 3.0 | Pass |
| Myclobutanil | 0.14 | 0.10 | Fail | 1.0 | Pass |
| Naled | 0.18 | 0.50 | Pass | 5.0 | Pass |
| Oxamyl | 0.15 | 2.00 | Pass | 15.0 | Pass |
| Pentachloronitrobenzene | 0.21 | 1.00 | Pass | 0.1 | Fail |
| Permethrin, Cis- | 0.07 | 0.10 | Pass | 9.0 | Pass |
| Permethrin, Trans- | 0.15 | 0.10 | Fail | 0.5 | Pass |
| Phosmet | 0.14 | 0.50 | Pass | 0.2 | Pass |
| Piperonyl butoxide | ND | 0.10 | Pass | 0.2 | Pass |
| Prallethrin | 0.13 | 0.50 | Pass | 20.0 | Pass |
| Propiconazole | 0.07 | 0.50 | Pass | 20.0 | Pass |
| Pyrethrins | 0.28 | 0.10 | Fail | 0.2 | Fail |
| Pyridaben | 0.10 | 3.00 | Pass | 8.0 | Pass |
| Spinetoram | 0.09 | 0.10 | Pass | 0.4 | Pass |
| Spinosyn A (Spinosad) | 0.09 | 0.10 | Pass | 20.0 | Pass |
| Spinosyn D (Spinosad) | 0.05 | 0.50 | Pass | 1.0 | Pass |
| Spiromesifen | 0.06 | 0.10 | Pass | 3.0 | Pass |
| Spirotetramat | 0.50 | 0.10 | Fail | 3.0 | Pass |
| Tebuconazole | 0.35 | 0.10 | Fail | 3.0 | Pass |
| Thiamethoxam | 1.71 | 0.10 | Fail | 3.0 | Pass |
| Trifloxystrobin | ND | 0.10 | Pass | 12.0 | Pass |
| | 0.06 | 0.10 | Pass | 13.0 | Pass |
| Mycotoxin Screen SOP: [SLW-MA] Method: LCMSMS ESI+ Dilute & Shoot | 0.09 | 0.10 | Pass | 2.0 | Pass |
| | 0.20 | 5.00 | Pass | 4.5 | Pass |
| Target Analyte Aflatoxin Total Ochratoxin A | 0.08 | 0.10 | Pass | 30.0 | Pass |

| | | California Limit | |
|---|---|---|---|
| | | Inhaled Product | Non-Inhaled Product |
| | PPM | PPM Pass/Fail | PPM Pass/Fail |
| Potency Test Result SOP: [SLW-CC] Method: HPLC-DAD American Herbal Pharmacopoeia | NT | 0.02 NT | 0.02 NT |
| Target Analyte % Test mg/g CBDA CBGA CBG CBD | NT | 0.02 NT | 0.02 NT |

Potency Summary

| | | | | |
|---|---|---|---|---|
| THCV | 0.19 | 1.90 | Total Calculated Δ9-THC (%)* | ND |
| CBN | ND | ND | | |
| THCA | 89.00 | 889.98 | Total Calculated CBD | 0.17 |
| Delta 9-THC (Δ9-THC) | ND | ND | | |
| Delta 8-THC (Δ8-THC) | ND | ND | Total Cannabinoids (%) | 89.19 |
| CBC | ND | ND | | |
| | ND | ND | | |
| Calculated in accordance with § 5724. of CA Code of Regulations Title 16 | ND | ND | | |
| Residual Solvent Test Results - Category 1 [SLW-RS] | ND | ND | | |
| Target Analyte PPM PPM Pass/Fail 1,2-Dichloroethane Benzene Chloroform | ND | ND | | |

California Limit - All products

| | | | |
|---|---|---|---|
| Ethylene oxide | | | |
| Methylene chloride | NT | 1.00 | NT |
| Trichloroethylene | NT | 1.00 | NT |
| | NT | 1.00 | NT |

TABLE 1-continued

Cleaned spike CBD after one wash, with all of the pesticides reduced.

Report of Analysis Revision

| | | | | | |
|---|---|---|---|---|---|
| Residual Solvent Test Results - Category 2 [SLW-RS] | NT | 1.00 | NT | | |
| | NT | 1.00 | NT | | |
| Target Analyte PPM | NT | 1.00 | NT | | |
| PPM Pass/Fail | | | | | |
| Acetone | | | | | |
| Acetonitrile | | California Limit | | | |
| Butane | | Cannabis Product or Pre-Roll | | | |
| Ethanol | | | | | |
| Ethyl acetate | NT | 5000 | NT | | |
| Ethyl ether | NT | 410 | NT | | |
| Heptane | NT | 5000 | NT | | |
| Hexane | NT | 5000 | NT | | |
| Isopropyl Alcohol | NT | 5000 | NT | | |
| Methanol | NT | 5000 | NT | | |
| Pentane | NT | 5000 | NT | | |
| Propane | NT | 290 | NT | | |
| Toluene | NT | 5000 | NT | | |
| Total Xylenes | NT | 3000 | NT | | |
| | NT | 5000 | NT | | |
| Microbial Screen SOP: [SLW-MS] qPCR PathoSEEK ™ | NT | 5000 | NT | | |
| Microbiological Assay Threshold Pass/Fail | NT | 890 | NT | | |
| *Salmonella* | NT | 2170 | NT | | |
| *Escherichia coli* (STEC) | | | | | |
| *Aspergillus niger* | | California Limit | | | |
| *Aspergillus fumigatus* | | | | | |
| *Aspergillus flavus* | NT | Detect/1 gram | NT | | |
| *Aspergillus terreus* | NT | Detect/1 gram | NT | | |
| Total Yeast and Mold* | NT | Detect/1 gram | NT | | |
| Total Aerobic Bacteria* | NT | Detect/1 gram | NT | | |
| Total *Enterobacteriaceae*\* | NT | Detect/1 gram | NT | | |
| Total Coliform Bacteria* | NT | Detect/1 gram | NT | | |
| *Escherichia coli* (Non-STEC)* | NT | 10000 CFU/g | NT | | |
| | NT | 100000 CFU/g | NT | | |
| Heavy Metals Screen SOP: [SLW-HMA] Method: ICPMS Target Analyte PPM | NT | 1000 CFU/g | NT | | |
| | NT | 1000 CFU/g | NT | | |
| Cadmium | NT | Detect/1 gram | NT | | |
| Lead | | | | | |
| Arsenic | | California Limit | | | |
| Mercury | | Inhaled Product PPM Pass/Fail | | Non-Inhaled Product PPM Pass/Fail | |
| | NT | 0.2 | NT | 0.5 | NT |
| Terpene Test Result SOP: [SLW-TA] GCFID | NT | 0.5 | NT | 0.5 | NT |
| Target Analyte % Test mg/g | NT | 0.2 | NT | 1.5 | NT |
| alpha-Bisabolol | NT | 0.1 | NT | 3.0 | NT |
| Camphene | | | | | |
| delta-3-Carene | | Terpene Summary | | | |
| beta-Caryophyllene | | | | | |
| Caryophyllene Oxide | NT | NT | Total Terpenes (%) | | |
| p-Cymene | NT | NT | NT | | |
| Geraniol | NT | NT | | | |
| Guaiol | NT | NT | | | |

TABLE 1-continued

Cleaned spike CBD after one wash, with all of the pesticides reduced.

Report of Analysis Revision

| | | |
|---|---|---|
| alpha-Humulene | NT | NT |
| Isopulegol | NT | NT |
| delta-Limonene | NT | NT |
| Linalool | NT | NT |
| beta-Myrcene | NT | NT |
| Nerolidol 1 | NT | NT |
| Nerolidol 2 | NT | NT |
| beta-Ocimene | NT | NT |
| alpha-Ocimene | NT | NT |
| alpha-Pinene | NT | NT |
| beta-Pinene | NT | NT |
| alpha-Terpinene | NT | NT |
| Gamma-Terpinene | NT | NT |
| Terpinolene | NT | NT |
| | NT | NT |
| | NT | NT |
| | NT | NT |
| results | NT | NT |

*All cannabinoid

ND = None Detected, NT = Not Tested, N/A = Not Applicable, <LOQ = Less than Limit of Quantitation, LOD = Limit of Detection

TABLE 2

Cleaned spiked CBD with pesticides.

Report of Analysis Revision

| | | | | |
|---|---|---|---|---|
| Manufacturer: | CRFT Manufacturing | | | |
| Manufacturer Address: | 2330 Circadian Way, Santa Rosa, CA | 95407 | | |
| Manufacturer License #: | CDPH-T00000329 | | | |
| Report #: | N9909 | | | |
| Sample Code: | 6633 | | | |
| Dates of Analysis: | May 10, 2019-May 17, 2019 | | | |
| Sample Matrix: | Extract | | | |
| Sample Name: | CBD D | | | |
| Percent Moisture (%) | NT | | California Limit | |
| SOP: [SLW-MCWA] Moisture Analyzer | NT | | NT | |
| Water Activity ($A_w$) | NT | $0.65 A_w$ | | NT |
| SOP: [SLW-MCWA] Moisture Analyzer | | | | |
| Pesticide Screen Result - Category 1 [SLW-PA] | | California Limit - Detect/No Detect All products | | |
| Target Analyte | PPM | LOD | LOQ | Pass/Fail |
| Aldicarb | 3.0 | 0.05 | 0.10 | Fail |
| Carbofuran | 3.1 | 0.05 | 0.10 | Fail |
| Chlordane | 0.5 | 0.05 | 0.10 | Fail |
| Chlorfenapyr | 1.7 | 0.05 | 0.10 | Fail |
| Chlorpyrifos | 3.3 | 0.05 | 0.10 | Fail |
| Coumaphos | 4.0 | 0.05 | 0.10 | Fail |
| Daminozide | 4.3 | 0.05 | 0.10 | Fail |
| Dichlorvos | 2.9 | 0.05 | 0.10 | Fail |
| Dimethoate | 3.0 | 0.05 | 0.10 | Fail |
| Ethoprop(hos) | 3.2 | 0.05 | 0.10 | Fail |
| Etofenprox | 3.7 | 0.05 | 0.10 | Fail |
| Fenoxycarb | 3.7 | 0.05 | 0.10 | Fail |
| Fipronil | 3.0 | 0.05 | 0.10 | Fail |
| Imazalil | 4.0 | 0.05 | 0.10 | Fail |
| Methiocarb | 3.3 | 0.05 | 0.10 | Fail |
| Methyl Parathion | 0.5 | 0.05 | 0.10 | Fail |
| Mevinphos | 2.7 | 0.05 | 0.10 | Fail |
| Paclobutrazol | 3.7 | 0.05 | 0.10 | Fail |
| Propoxur | 2.8 | 0.05 | 0.10 | Fail |

TABLE 2-continued

Cleaned spiked CBD with pesticides.

Report of Analysis Revision

| | | | | |
|---|---|---|---|---|
| Spiroxamine | 3.4 | 0.05 | 0.10 | Fail |
| Thiacloprid | 2.9 | 0.05 | 0.10 | Fail |

| Pesticide Screen Category 2 [SLW-PA] | | California Limit | | |
|---|---|---|---|---|
| | | Inhaled Product | | Non-Inhaled Product |
| Target Analyte | PPM | PPM | Pass/Fail | PPM | Pass/Fail |

| Target Analyte | PPM | PPM | Pass/Fail | PPM | Pass/Fail |
|---|---|---|---|---|---|
| Acephate | 3.01 | 0.10 | Fail | 5.0 | Pass |
| Acequinocyl | 1.30 | 0.10 | Fail | 4.0 | Pass |
| Acetamiprid | 3.07 | 0.10 | Fail | 5.0 | Pass |
| Avermectin B1a (Abamectin) | 2.77 | 0.10 | Fail | 0.3 | Fail |
| Avermectin B1b (Abamectin) | 3.68 | 0.10 | Fail | 0.3 | Fail |
| Azoxystrobin | 4.26 | 0.10 | Fail | 40.0 | Pass |
| Bifenazate | 3.74 | 0.10 | Fail | 5.0 | Pass |
| Bifenthrin | 3.25 | 3.00 | Fail | 0.5 | Fail |
| Boscalid | 3.66 | 0.10 | Fail | 10.0 | Pass |
| Captan | ND | 0.70 | Pass | 5.0 | Pass |
| Carbaryl | 3.76 | 0.50 | Fail | 0.5 | Fail |
| Chlorantraniliprole | 10.44 | 10.00 | Fail | 40.0 | Pass |
| Clofentezine | 2.58 | 0.10 | Fail | 0.5 | Fail |
| Cyfluthrin | 0.28 | 2.00 | Pass | 1.0 | Pass |
| Cypermethrin | 0.69 | 1.00 | Pass | 1.0 | Pass |
| Diazinon | 4.54 | 0.10 | Fail | 0.2 | Fail |
| Dimethomorph | 4.43 | 2.00 | Fail | 20.0 | Pass |
| Etoxazole | 3.79 | 0.10 | Fail | 1.5 | Fail |
| Fenhexamid | 3.08 | 0.10 | Fail | 10.0 | Pass |
| Fenpyroximate | 3.91 | 0.10 | Fail | 2.0 | Fail |
| Flonicamid | 2.99 | 0.10 | Fail | 2.0 | Fail |
| Fludioxonil | 3.25 | 0.10 | Fail | 30.0 | Pass |
| Hexythiazox | 3.39 | 0.10 | Fail | 2.0 | Fail |
| Imidacloprid | 3.31 | 5.00 | Pass | 3.0 | Fail |
| Kresoxim-methyl | 3.28 | 0.10 | Fail | 1.0 | Fail |
| Malathion | 3.41 | 0.50 | Fail | 5.0 | Pass |
| Metalaxyl | 3.64 | 2.00 | Fail | 15.0 | Pass |
| Methomyl | 3.21 | 1.00 | Fail | 0.1 | Fail |
| Myclobutanil | 3.64 | 0.10 | Fail | 9.0 | Pass |
| Naled | 3.49 | 0.10 | Fail | 0.5 | Fail |
| Oxamyl | 3.01 | 0.50 | Fail | 0.2 | Fail |
| Pentachloronitrobenzene | 0.40 | 0.10 | Fail | 0.2 | Fail |
| Permethrin, Cis- | 3.34 | 0.50 | Fail | 20.0 | Pass |
| Permethrin, Trans- | 3.99 | 0.50 | Fail | 20.0 | Pass |
| Phosmet | 4.11 | 0.10 | Fail | 0.2 | Fail |
| Piperonyl butoxide | 3.08 | 3.00 | Fail | 8.0 | Pass |
| Prallethrin | 3.92 | 0.10 | Fail | 0.4 | Fail |
| Propiconazole | 3.63 | 0.10 | Fail | 20.0 | Pass |
| Pyrethrins | 4.40 | 0.50 | Fail | 1.0 | Fail |
| Pyridaben | 3.80 | 0.10 | Fail | 3.0 | Fail |
| Spinetoram | 3.46 | 0.10 | Fail | 3.0 | Fail |
| Spinosyn A (Spinosad) | 2.41 | 0.10 | Fail | 3.0 | Pass |
| Spinosyn D (Spinosad) | 10.49 | 0.10 | Fail | 3.0 | Fail |
| Spiromesifen | 0.97 | 0.10 | Fail | 12.0 | Pass |
| Spirotetramat | 2.31 | 0.10 | Fail | 13.0 | Pass |
| Tebuconazole | 3.67 | 0.10 | Fail | 2.0 | Fail |
| Thiamethoxam | 3.18 | 5.00 | Pass | 4.5 | Pass |
| Trifloxystrobin | 3.49 | 0.10 | Fail | 30.0 | Pass |

| Mycotoxin Screen SOP: [SLW-MA] Method: LCMSMS ESI+ Dilute & Shoot | | California Limit | | | |
|---|---|---|---|---|---|
| | | Inhaled Product | | Non-Inhaled Product | |
| Target Analyte | PPM | PPM | Pass/Fail | PPM | Pass/Fail |
| Aflatoxin Total | NT | 0.02 | NT | 0.02 | NT |
| Ochratoxin A | NT | 0.02 | NT | 0.02 | NT |

| Potency Test Result SOP: [SLW-CC] Method: HPLC-DAD American Herbal Pharmacopoeia | | Potency Summary | |
|---|---|---|---|
| Target Analyte | % Test | mg/g | |
| CBDA | 0.35 | 3.49 | Total | 2.75 |
| CBGA | ND | ND | Calculated 59-THC (%)* | |
| CBG | 1.27 | 12.68 | Total | 69.77 |
| CBD | 69.46 | 694.59 | Calculated CBD | |
| THCV | ND | ND | Total | 73.93 |
| CBN | 0.04 | 0.39 | Cannabinoids (%) | |

TABLE 2-continued

Cleaned spiked CBD with pesticides.

Report of Analysis Revision

| | | |
|---|---|---|
| THCA | ND | ND |
| Delta 9-THC (δ9-THC) | 2.75 | 27.45 |
| Delta 8-THC (δ8-THC) | ND | ND |
| CBC | 0.07 | 0.67 | calculated in accordance with § 5724. of CA Code of Regulations Title 16

| Residual Solvent Test Results - Category 1 [SLW-RS] | | California Limit - All products | |
|---|---|---|---|
| Target Analyte | PPM | PPM | Pass/Fail |
| 1,2-Dichloroethane | NT | 1.00 | NT |
| Benzene | NT | 1.00 | NT |
| Chloroform | NT | 1.00 | NT |
| Ethylene oxide | NT | 1.00 | NT |
| Methylene chloride | NT | 1.00 | NT |
| Trichloroethylene | NT | 1.00 | NT |

| Residual Solvent Test Results - Category 2 [SLW-RS] | | California Limit Cannabis Product or Pre-Roll | |
|---|---|---|---|
| Target Analyte | PPM | PPM | Pass/Fail |
| Acetone | NT | 5000 | NT |
| Acetonitrile | NT | 410 | NT |
| Butane | NT | 5000 | NT |
| Ethanol | NT | 5000 | NT |
| Ethyl acetate | NT | 5000 | NT |
| Ethyl ether | NT | 5000 | NT |
| Heptane | NT | 5000 | NT |
| Hexane | NT | 290 | NT |
| Isopropyl Alcohol | NT | 5000 | NT |
| Methanol | NT | 3000 | NT |
| Pentane | NT | 5000 | NT |
| Propane | NT | 5000 | NT |
| Toluene | NT | 890 | NT |
| Total Xylenes | NT | 2170 | NT |

| Microbial Screen SOP: [SLW-MS] qPCR PathoSEEK ™ | | California Limit | |
|---|---|---|---|
| Microbiological Assay | | Threshold | Pass/Fail |
| *Salmonella* | NT | Detect/1 gram | NT |
| *Escherichia coli* (STEC) | NT | Detect/1 gram | NT |
| *Aspergillus niger* | NT | Detect/1 gram | NT |
| *Aspergillus fumigatus* | NT | Detect/1 gram | NT |
| *Aspergillus flavus* | NT | Detect/1 gram | NT |
| *Aspergillus terreus* | NT | Detect/1 gram | NT |
| Total Yeast and Mold* | NT | 10000 CFU/g | NT |
| Total Aerobic Bacteria* | NT | 100000 CFU/g | NT |
| Total *Enterobacteriaceae** | NT | 1000 CFU/g | NT |
| Total Coliform Bacteria* | NT | 1000 CFU/g | NT |
| *Escherichia coli* (Non-STEC)* | NT | Detect/1 gram | NT |

| Heavy Metals Screen SOP: [SLW-HMA] Method: ICPMS | | California Limit | | | |
|---|---|---|---|---|---|
| | | Inhaled Product | | Non-Inhaled Product | |
| Target Analyte | PPM | PPM | Pass/Fail | PPM | Pass/Fail |
| Cadmium | NT | 0.2 | NT | 0.5 | NT |
| Lead | NT | 0.5 | NT | 0.5 | NT |
| Arsenic | NT | 0.2 | NT | 1.5 | NT |
| Mercury | NT | 0.1 | NT | 3.0 | NT |

| Terpene Test Result SOP: [SLW-TA] GCFID | | Terpene Summary | |
|---|---|---|---|
| Target Analyte | % | Test | mg/g |
| alpha-Bisabolol | NT | NT | Total Terpenes (%) NT |
| Camphene | NT | NT | |

TABLE 2-continued

Cleaned spiked CBD with pesticides.

Report of Analysis Revision

| | | |
|---|---|---|
| delta-3-Carene | NT | NT |
| beta-Caryophyllene | NT | NT |
| Caryophyllene Oxide | NT | NT |
| p-Cymene | NT | NT |
| Geraniol | NT | NT |
| Guaiol | NT | NT |
| alpha-Humulene | NT | NT |
| Isopulegol | NT | NT |
| delta-Limonene | NT | NT |
| Linalool | NT | NT |
| beta-Myrcene | NT | NT |
| Nerolidol 1 | NT | NT |
| Nerolidol 2 | NT | NT |
| beta-Ocimene | NT | NT |
| alpha-Ocimene | NT | NT |
| alpha-Pinene | NT | NT |
| beta-Pinene | NT | NT |
| alpha-Terpinene | NT | NT |
| Gamma-Terpinene | NT | NT |
| Terpinolene | NT | NT |
| results | | |

*All cannabinoid

ND = None Detected, NT = Not Tested, N/A = Not Applicable, <LOQ = Less than Limit of Quantitation, LOD = Limit of Detection

TABLE 3

Cleaned THCA/THC with all the pesticides

| Pesticide Screen Result - Category 1 Target Analyte | PPM < ug/g) | LOO(ug/g) | LOQWo) | Califonia Limit - All Products Pass/Fail |
|---|---|---|---|---|
| Aldicarb | ND | 0.02 | 0.08 | Pass |
| Carbofuran | ND | 0.02 | 0.08 | Pass |
| Chlordane | ND | 0.05 | 0.1 | Pass |
| Chlorfenapyr | ND | 0.05 | 0.1 | Pass |
| Chlorphynfos | ND | 0.02 | 0.08 | Pass |
| Coumaphos | ND | 0.02 | 0.08 | Pass |
| Damlnozide | ND | 0.02 | 0.08 | Pass |
| Dicholonos | ND | 0.02 | 0.08 | Pass |
| Dimethoate | ND | 0.02 | 0.08 | Pass |
| Ethoprod(hos) | ND | 0.02 | 0.08 | Pass |
| Etofenprox | ND | 0.02 | 0.08 | Pass |
| Fenoxycarb | ND | 0.02 | 0.08 | Pass |
| Fipronil | ND | 0.02 | 0.08 | Pass |
| Imazalil | ND | 0.02 | 0.08 | Pass |
| Methiocarb | ND | 0.02 | 0.08 | Pass |
| Methyl Paratholon | ND | 0.05 | 0.1 | Pass |
| Mevinphos | ND | 0.02 | 0.08 | Pass |
| Paclobutrazol | ND | 0.02 | 0.08 | Pass |
| Propoxur | ND | 0.02 | 0.08 | Pass |
| Spiroxamine | ND | 0.02 | 0.08 | Pass |
| Thiacloprid | ND | 0.02 | 0.08 | Pass |

| Pesticide Screen Result - Category 2 Target Analyte | PPM (ug/g) | LOD (ug/g) | LOQ (ug/g) | PPM (ug/g) | Califonia Limit - All Products Pass/Fail |
|---|---|---|---|---|---|
| Aceptote | ND | 0.02 | 0.08 | 0.1 | Pass |
| Acequinocyt | ND | 0.02 | 0.08 | 0.1 | Pass |
| Acetamiprid | ND | 0.02 | 0.02 | 0.1 | Pass |
| Avemveciln B1a (Abamoctin) | ND | 0.02 | 0.08 | 0.1 | Pass |
| Avermectin B1b (Abamectin) | ND | 0.1 | 0.2 | 0.1 | Pass |
| Azoxystrobin | ND | 0.02 | 0.08 | 0.1 | Pass |
| Bifenarato | ND | 0.02 | 0.08 | 0.1 | Pass |
| Bifenthrin | ND | 0.02 | 0.08 | 3 | Pass |
| Boscalid | ND | 0.02 | 0.08 | 0.1 | Pass |
| Captan | ND | 0.12 | 0.2 | 0.7 | Pass |
| Carbaryl | ND | 0.02 | 0.08 | 0.5 | Pass |
| Choarnthrniliprole | ND | 0.02 | 0.08 | 10 | Pass |
| Clofontozine | ND | 0.02 | 0.08 | 0.1 | Pass |
| Cyfluthrin | ND | 0.02 | 0.1 | 2 | Pass |
| Cypermethrin | ND | 0.05 | 0.1 | 1 | Pass |

TABLE 3-continued

Cleaned THCA/THC with all the pesticides

| | | | | | |
|---|---|---|---|---|---|
| Diazinon | ND | 0.02 | 0.08 | 0.1 | Pass |
| Dimelhomorph | ND | 0.02 | 0.08 | 2 | Pass |
| Etoxazoio | ND | 0.02 | 0.08 | 0.1 | Pass |
| Fenhexamid | ND | 0.02 | 0.08 | 0.1 | Pass |
| Fenpiyoximato | ND | 0.02 | 0.08 | 0.1 | Pass |
| Flonicamid | ND | 0.02 | 0.08 | 0.1 | Pass |
| Fludioxonil | ND | 0.02 | 0.08 | 0.1 | Pass |
| Hexythiazox | ND | 0.02 | 0.08 | 0.1 | Pass |
| Imdiadoprid | ND | 0.02 | 0.08 | 5 | Pass |
| Krosoxim-methyl | ND | 0.02 | 0.08 | 0.1 | Pass |
| Malathion | ND | 0.02 | 0.08 | 0.5 | Pass |
| Methomyl | ND | 0.02 | 0.08 | 0.1 | Pass |
| Myclobutanil | ND | 0.02 | 0.08 | 0.1 | Pass |
| Naled | ND | 0.02 | 0.08 | 0.1 | Pass |
| Oxamyl | ND | 0.02 | 0.08 | 0.5 | Pass |
| Pentachloronitrobenzene | ND | 0.02 | 0.05 | 0.1 | Pass |
| Pennethrine, Cis- | ND | 0.02 | 0.08 | 0.S | Pass |
| Pennethrine, Trans- | ND | 0.02 | 0.08 | 0.5 | Pass |
| Phosmet | ND | 0.02 | 0.08 | 0.1 | Pass |
| Piperonytbutoxide | ND | 0.02 | 0.08 | 0.1 | Pass |
| Prilethrin | ND | 0.02 | 0.08 | 0.1 | Pass |
| Propiconazole | ND | 0.02 | 0.08 | 0.1 | Pass |
| Pyrethrines | ND | 0.02 | 0.08 | 0.1 | Pass |
| Paraben | ND | 0.02 | 0.08 | 0.1 | Pass |
| Sptoetoram | ND | 0.02 | 0.08 | 0.1 | Pass |
| Spinosyn A (Spinosa) | ND | 0.02 | 0.08 | 0.1 | Pass |
| Spinosyn D (Spinosa) | ND | 0.08 | 0.16 | 0.1 | Pass |
| Tebuconazole | ND | 0.02 | 0.08 | 0.08 | Pass |
| Thiamethoxam | ND | 0.02 | 0.08 | 0.1 | Pass |
| Trifloxystrobin | ND | 0.02 | 0.08 | 5 | Pass |

TABLE 4

Pesticides screen results (pesticides reduced by two folds after the second hexane wash).

| Pesticide Screen Result Concentration Target Analyte | Oregon Pass/Fail | Concen- tration (PPM) | Oregon Limit Concentration (PPM) | LOD Concentration (PPB) |
|---|---|---|---|---|
| Acequlnocyl | ND | ND | 2 | 30 |
| Avermectin Bla (Abamectin) | ND | ND | 0.5 | 0.15 |
| Avermectin Bib (Abamectin) | ND | 0.15 | | |
| Brfenazate | BDL | BDL | 0.2 | 0.15 |
| Bifenthrin | ND | ND | 0.2 | 0.15 |
| Boscalid | ND | ND | 0.4 | 0.15 |
| Carbaryl | ND | ND | 0.2 | 0.15 |
| Damlnozlde | ND | ND | 1 | 30 |
| Etoxazole | ND | ND | 0.2 | 0.15 |
| Fenoxycarb | ND | ND | 0.2 | 0.15 |
| Fenpyroxlmate | ND | ND | 0.4 | 0.15 |
| Imazalil | ND | ND | 0.2 | 0.15 |
| Imidacloprid | ND | ND | 0.4 | 0.15 |
| Kresoxim-methyl | ND | ND | 0.4 | 0.15 |
| Malathion A | ND | ND | 0.2 | 0.15 |
| Metalaxyl | ND | ND | 0.2 | 0.15 |
| Myclobutanil | Fail | 4.443 | 0.2 | 0.15 |
| Paclobutrazol | ND | ND | 0.4 | 0.15 |
| Permethrin, cis- | ND | ND | 0.2 | 0.15 |
| Permethrin, trans- | ND | 0.15 | | |
| Piperonyl butoxide | Pass | 0.066 | 2 | 0.15 |
| Propiconazole | ND | ND | 0.4 | 0.15 |
| Spinosyn A (Spinosad) | ND | ND | 0.2 | 0.06 |
| Spfnosyn D (Spinosad) | ND | 0.06 | | |
| Spiromesifen | ND | ND | 0.2 | 0.15 |
| Spirotetramat | BDL | BDL | 0.2 | 0.15 |
| Tebuconazole | ND | ND | 0.4 | 0.06 |
| Trifloxystrobin | ND | ND | 0.2 | 0.06 |

'There are no current industry guidelines set in the state of California regarding pesticide residue limits on cannabis. The presence of pesticides is determined by our facility's lowest quantifiable and distinguishable limit.
**Oregon Reporting limits are net applicable in the state of California. They are provided as reference only.

What is claimed is:

1. A method for removing one or more pesticides from a *cannabis* product comprising:
    acetylating or carboxylating a *cannabis* product;
    dissolving, in a solvent, the *cannabis* product including one or more pesticides, forming a dissolved solution;
    cooling the dissolved solution to a cooling temperature to cause the *cannabis* product to precipitate from the dissolved solution, wherein, at the cooling temperature, the one or more pesticides remain dissolved in the dissolving solution; and
    removing the precipitated *cannabis* product from the dissolving solution.

2. A method for removing one or more pesticides from an acetylated or carboxylated *cannabis* product, comprising:
    dissolving, in a solvent, an acetylated or carboxylated *cannabis* product including one or more pesticides, forming a dissolved solution;
    cooling the dissolved solution to a cooling temperature to cause the *cannabis* product to precipitate from the dissolved solution, wherein, at the cooling temperature, the one or more pesticides remain dissolved in the dissolving solution.

3. The method of claim 1, further comprising: after the step of removing, washing the precipitated *cannabis* product with the solvent one or more secondary times.

4. The method of claim 1, further comprising removing any remaining solvent in a reduced pressure.

5. The method of claim 1, wherein the cooling temperature is between about 0° C. and about 100° C.

6. The method of claim 1, wherein steps of dissolving, cooling, and removing are repeated until the resulting *cannabis* product has a purity of about 85%.

7. The method of claim 1, wherein steps of dissolving, cooling, and removing are repeated until the resulting *cannabis* product has a purity of about 95%.

8. The method of claim 1, wherein the solvent comprises one or more solvents selected from the group consisting of: hydrocarbons; aromatics; halogenated organic solvents; amines; and acetates.

9. The method of claim 1, wherein the solvent is pentane.

10. The method of claim 1, wherein the *cannabis* product comprises one or more cannabinoids selected from the group consisting of: tetrahydrocannabinol (THC), cannabidiol (CBD), Cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

11. The method of claim 10, wherein the *cannabis* product comprises an acetylated analog or a carboxylated analog of the one or more cannabinoids.

12. The method of claim 10, wherein the *cannabis* product comprises THC.

13. The method of claim 2, wherein the acetylated or carboxylated *cannabis* product comprises THCA.

14. The method of claim 1, wherein the *cannabis* product is a distillate *cannabis* product.

15. A method for removing one or more pesticides from a *cannabis* product, comprising:
(a) mixing a first solvent with a *cannabis* product comprising an acetylated or carboxylated *cannabis* product,
(b) mixing the resulting solution with a second solvent comprising acetonitrile, thereby causing one or more pesticides to partition into a solvent layer containing the second solvent; and
(c) removing the solvent layer containing the second solvent so that the resulting *cannabis* product contains a reduced amount of one or more pesticides.

16. The method of claim 15, further comprising repeating steps (a)-(c) at least once.

17. The method of claim 15, wherein the first solvent comprises hexane.

18. The method of claim 15, wherein the first solvent and the second solvent have a ratio of 1:2 (v/v).

19. The method of claim 1, further comprising adding an additive, a pharmaceutical acceptable carrier, or an adjuvant to the *cannabis* product.

20. The method of claim 19, further comprising adding a second agent selected from the group consisting of: cannabinoids, terpenes, anti-insomnia, anti-tussive, opiod analgesic, decongestant, non-opioid analgesic/anti-inflammatory drug, anti-migraine drug, anti-emetic, anti-histamine, proton pump inhibitor, H2 antagonist/H2 blocker, tranquilizer, anticonvulsant, hypnotic, muscle relaxant, anti-psychotic, antidiarrheal, Attention Deficit and Hyperactivity Disorder (ADHD) drug, anti-Parkinson disease drug, benzodiazepine, benzodiazepine antagonist, barbiturate, barbiturate antagonist, stimulant, stimulant antagonist, antidepressant, nutraceutical, nicotine, BCS Class II active ingredient, BCS Class IV active ingredient, an anti-multiple sclerosis (MS) drug, ethyl pyruvate, melatonin, caffeine, resveratrol, and a combination thereof to the *cannabis* product.

21. The method of claim 20, wherein the second agent is selected from the group consisting of: CBD, THC, CBN, CBG, CBC, THCA, CBDA, THCV, and a combination thereof.

22. The method of claim 1, wherein the *cannabis* product is an oral dosage composition, a pulmonary or nasal dosage composition, or a topical dosage composition.

23. The method of claim 1, wherein the *cannabis* product is in the form of a solution, a spray, or a powder, a tablet, a capsule, a jelly, a cream, an ointment, a suspension, or a chewing gum.

24. The method of claim 1, wherein the *cannabis* product comprises an edible product.

25. The method of claim 24, wherein the edible product is selected from a lozenge, candy, chocolate, brownie, cookie, trail bar, cracker, dissolving strip, pastry, bread, or chewing gum.

\* \* \* \* \*